(12) United States Patent
Dextradeur et al.

(10) Patent No.: US 8,221,392 B2
(45) Date of Patent: Jul. 17, 2012

(54) FLUID MANAGEMENT FLOW IMPLANTS OF IMPROVED OCCLUSION RESISTANCE

(75) Inventors: Alan Dextradeur, Franklin, MA (US); Christophe Mauge, Melrose, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 706 days.

(21) Appl. No.: 11/931,024

(22) Filed: Oct. 31, 2007

(65) Prior Publication Data
US 2008/0214982 A1   Sep. 4, 2008

(51) Int. Cl.
*A61M 5/00* (2006.01)
*A61M 1/00* (2006.01)

(52) U.S. Cl. .......................... 604/540; 604/8

(58) Field of Classification Search ............. 604/266, 604/537, 8, 43, 99.02, 99.04, 131, 246, 264, 604/265, 540
See application file for complete search history.

(56) References Cited

U.S. PATENT DOCUMENTS

| | | |
|---|---|---|
| 3,601,128 A | 8/1971 | Hakim |
| 3,669,116 A | 6/1972 | Heyer |
| 3,690,323 A | 9/1972 | Wortman |
| 3,894,541 A | 7/1975 | El-Shafei |
| 4,182,343 A | 1/1980 | Inaba |
| 4,377,169 A | 3/1983 | Banks |
| 4,655,745 A | 4/1987 | Corbett |
| 4,767,400 A | 8/1988 | Miller |
| 4,917,686 A | 4/1990 | Bayston |
| 4,950,232 A | 8/1990 | Ruzicka |
| 5,180,387 A | 1/1993 | Ghajar |
| 5,405,316 A | 4/1995 | Magram |
| 5,451,215 A | 9/1995 | Wolter |
| 5,531,673 A | 7/1996 | Helenowski |
| 5,579,774 A | 12/1996 | Miller |
| 6,110,155 A | 8/2000 | Baudino |
| 6,325,815 B1 | 12/2001 | Kusleika |
| 6,350,253 B1 * | 2/2002 | Deniega et al. .......... 604/164.02 |
| 6,524,268 B2 | 2/2003 | Hayner |
| 6,533,763 B1 | 3/2003 | Schneiter |
| 6,626,885 B2 | 9/2003 | Massengale |
| 2002/0001609 A1 | 1/2002 | Calhoun |
| 2002/0032460 A1 | 3/2002 | Kusleika |
| 2002/0082547 A1 | 6/2002 | Deniega |
| 2002/0111601 A1 | 8/2002 | Thompson |
| 2002/0188246 A1 | 12/2002 | Hayner |
| 2003/0009132 A1 | 1/2003 | Schwartz |
| 2003/0073647 A1 | 4/2003 | Chao |

(Continued)

FOREIGN PATENT DOCUMENTS

EP          1364628 A1     11/2003

(Continued)

OTHER PUBLICATIONS

Lin, J; Morris, M; Olivero, W; Boop, F; Sanford, R: "Computational and experimental study of proximal flow in ventricular catheters" Journal of Neurosurgery, vol. 99, 2003, pp. 426-431, XP008082562.

(Continued)

*Primary Examiner* — Melanie Hand

(57) ABSTRACT

This invention relates to achieving or improving uniform distribution of fluid flow in medical devices such as when combined with antibiotics impregnated in a catheter and/or with a drug-eluting catheter to further inhibit the catheter from becoming occluded by debris in the CSF or by bacterial biofilm formation or tissue proliferation in the catheter.

11 Claims, 2 Drawing Sheets

U.S. PATENT DOCUMENTS

| | | |
|---|---|---|
| 2003/0216710 A1 | 11/2003 | Hurt |
| 2004/0054351 A1 | 3/2004 | Deniega |
| 2004/0253185 A1 | 12/2004 | Herweck |
| 2005/0153379 A1 | 7/2005 | Hoon |

FOREIGN PATENT DOCUMENTS

| | | |
|---|---|---|
| WO | 8703495 | 6/1987 |
| WO | 8904682 | 6/1989 |
| WO | WO 9407549 A1 * | 4/1994 |
| WO | 0105210 | 1/2001 |
| WO | WO 2004073768 A2 * | 9/2004 |

OTHER PUBLICATIONS

Bayston & Penny, Excessive Production of Mucoid Substance in Staphylococcus SIIA: a Possible Factor in Colonisation of Holter Shunts; Dev. Med. Child Neurol, 1972, pp. 25-28., 14 Suppl 27; UK.

Codman Product Brochure; Codman Bactiseal Antimicrobial Impregnated Catheter System; Codman & Shurtleff, 2002.

Codman Product Brochure; Codman Bactiseal EVD Catheter, Codman & Shurtleff, Inc., 2004.

Collins, P., et al., Surface ultrastructure of tissues occluding ventricular catheters; J. Neurosurg, Apr. 1978 pp. 609-613 vol. 48:, UK.

Del Bigio, M. And Brunt, J.E.; Reaction of rabbit lateral peri ventricular tissue to shunt tubing implants; J. Neurosurgery, Jun. 1986. pp. 932-940; vol. 64.

Del Bigio, M. And Fedoroff, S.; Short-term response of brain tissue to cerebrospinal fluid shunts in vivo and in vitro; J. Biomed Mater Res, 1992; pp. 979-987; vol. 26; 1992 John Wiley & Sons, Inc.

Del Bigio, M., Biological Reactions to Cerebrospinal Fluid Shunt Devices: A Review of the Cellular Pathology Topic Review; Neurosurgery, Feb. 1998, pp. 319-326; vol. 42 No. 2;.

Drake, J.M. and Sainte-Rose, C.; Shunt Complications; The Shunt Book, 1995, Chapt. 5; pp. 123-192. Blackwell Science; Cambridge, MA.

Drake, J.M. and Sainte-Rose, C.; Cerebrospinal Fluid Shunt Components The Shunt Book, 1995., Chapt. 4, pp. 71-119. Blackwell Science; Cambridge, MA.

Edvinsson, L., et al., Alterations in Intracranial Pressure, Blood-Brain Barrier, and Brain Edema after Sub-Chronic Implantation of a Cannula into the Brain of Conscious Animals; Acta Physiol Scand, 1971; pp. 527-531, vol. 82: Sweden.

Gotz, F. and Peters, G.; Colonization of Medical Devices by Coagulase-Negative Staphylococci; Infections Associated with Indwelling Medical Devices Third Edition; 2000; pp. 55-88; ASM Press, Washington DC.

Jaeger, C.B., et al.; Repair of the blood-brain barrier following implantation of polymer capsules; Brain Res, 1991; pp. 163-170, vol. 551. Elsevier Science Publishers B.V.

Kestle, J., et al., Long-Term Follow-Up Data from the Shunt Design Trial Pediatric Neurosurgery, 2000 pp. 230-236; vol. 33; S. Karger, AG, Switzerland www.karger.com/journals/pne.

Kossovsky, N. and Snow, R.B.; Clinical-pathological analysis of failed central nervous system fluid shunts; J. Biomed Mater Res. 1989; pp. 73-86; vol. 23, No. A1; John Wiley & Sons, Hoboken, NJ.

Lundberg, F., et al., Presence of vitronectin and activated complement factor C9 on ventriculoperitoneal shunts and temporary ventricular drainage catheters; J. Neurosurg, 1999, pp. 101-108; vol. 90:. American Association of Neurological Surgeons, Illinois.

Raftopoulos, C. et al., Brain Oedema Induced by Ventricular Puncture Acta Neurochir (Wien), 1994; pp. 177-180; vol. 129; Springer-Veriag, Austria.

Sainte-Rose, C., et al., Mechanical Complications in Shunts; Pediatric Neurosurgery, 1991; pp. 2-9; vol. 17; S. Karger, AG, Switzerland.

Takahashi, Y. et al., Ultrastructure of Obstructive Tissue in Malfunctioning Ventricular Catheters Without Infection; Neurol Med Chir. 1998; pp. 399-404; vol. 38., Tokyo.

\* cited by examiner

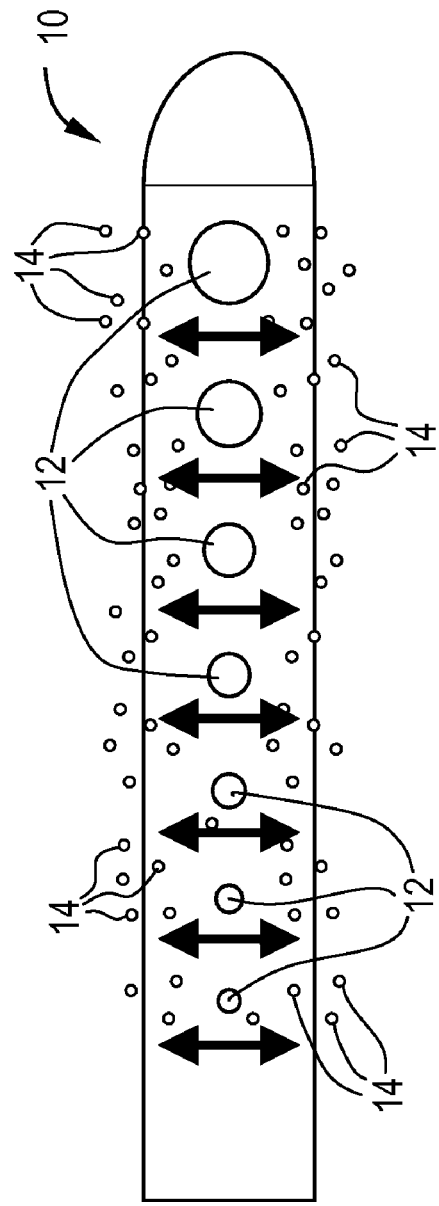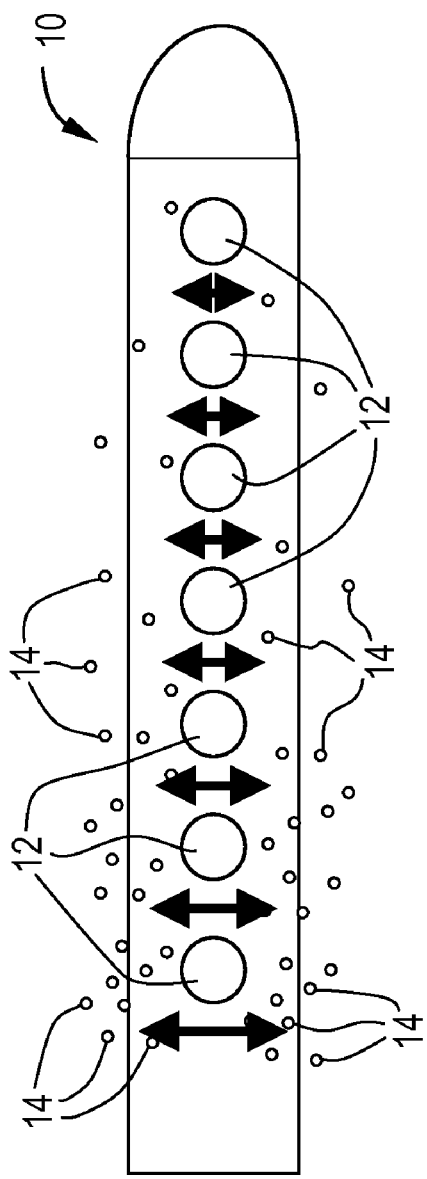

FLUID MANAGEMENT FLOW IMPLANTS OF IMPROVED OCCLUSION RESISTANCE

BACKGROUND OF THE INVENTION

1. Field of the Invention

The present invention relates to fluid management flow devices such as a catheter device and methods useful with such devices, and in particular hydrocephalus shunts containing an antibiotic and/or drug to minimize the risk of blockage or obstruction inside of the catheter while improving protection against colonization of gram-positive bacteria and/or tissue proliferation when the devices are combined with uniform fluid flow enhancing tips.

2. Related Art

Hydrocephalus is a neurological condition that is caused by the abnormal accumulation of cerebrospinal fluid (CSF) within the ventricles, or cavities, of the brain. CSF is a clear, colorless fluid that is primarily produced by the choroid plexus and surrounds the brain and spinal cord. CSF constantly circulates through the ventricular system of the brain and is ultimately absorbed into the bloodstream. CSF aids in the protection of the brain and spinal cord. Because CSF keeps the brain and spinal cord buoyant, it acts as a protective cushion or "shock absorber" to prevent injuries to the central nervous system.

Hydrocephalus, which affects children and adults, arises when the normal drainage of CSF in the brain is blocked in some way. Such blockage can be caused by a number of factors, including, for example, genetic predisposition, intraventricular or intracranial hemorrhage, infections such as meningitis, head trauma, or the like. Blockage of the flow of CSF consequently creates an imbalance between the amount of CSF produced by the choroid plexus and the rate at which CSF is absorbed into the bloodstream, thereby increasing pressure on the brain, which causes the ventricles to enlarge.

Some of these problems can be treated by backflushing, which is a process that uses the CSF present in the shunt system to remove the obstructing matter. This process can be ineffective, however, due to the small size of the pores of the ventricular catheter and due to the small amount of flushing liquid available in the shunt system. Other shunt systems have been designed to include a mechanism for flushing the shunt system. For example, some shunt systems include a pumping device within the system which causes fluid in the system to flow with considerable pressure and velocity, thereby flushing the system. As with the process of backflushing, using a built-in mechanism to flush the shunt system can also fail to remove the obstruction due to factors such as the size of the pores and the degree and extent to which the pores have been clogged.

Occluded ventricular catheters can also be repaired by cauterizing the catheter to remove blocking tissue, thereby reopening existing pores that have become occluded. Alternatively, new pores can be created in the catheter. These repairs, however, may be incapable of removing obstructions from the ventricular catheter depending on the location of the clogged pores. Additionally, the extent of tissue growth into and around the catheter can also preclude the creation of additional pores, for example, in situations where the tissue growth covers a substantial portion of the ventricular catheter. Another disadvantage of creating new apertures to repair an occluded ventricular catheter is that this method fails to prevent or reduce the risk of repeated obstructions.

Because attempts at flushing or repairing a blocked ventricular catheter are often futile and ineffective, occlusion is more often treated by replacing the catheter. Although this can be accomplished by simply removing the obstructed catheter from the ventricle, the growth of the choroid plexus and other tissues around the catheter and into the pores can hinder removal and replacement of the catheter. Care must be exercised to avoid damage to the choroid plexus, which can cause severe injury to the patient, such as, for example, hemorrhaging. Not only do these procedures pose a significant risk of injury to the patient, they can also be very costly, especially when shunt obstruction is a recurring problem U.S. Pat. No. 4,917,686, the disclosure of which is hereby incorporated by reference, describes implanted medical devices (such catheters, valves, molded parts, etc. and including hydrocephalus shunts and central venous catheters) that have been treated with antimicrobial agents to combat the problem of colonization of bacteria particularly on the interior surfaces of the device.

US 2003/0216710, the disclosure of which is whereby incorporated by reference, describes a catheter having one or more inlet holes along the length of the catheter whereby the cross-sectional areas of successive inlet holes decreases, the decrease first occurring at the inlet hole immediately following the most proximal inlet hole. Such a design purports to alter the typical inflow of fluid into the catheter such that a disproportionately high volume of fluid no longer enters the most proximal inlet hole. The decrease in inflow at the most proximal inlet results in less deposition of debris within the catheter at this position.

Lin et al., in "Computational and Experimental Study of Proximal Flow in Ventricular Catheters", (*J. Neurosurgery* 99:426-431, 2003), the disclosure of which is hereby incorporated by reference, describes and demonstrates that drainage hole geometry is indeed a factor in achieving uniform flow patterns within ventricular catheters. FIG. 2 of Lin dramatically demonstrates the flow distribution improvement when catheter hole geometry is modified. The problem addressed by Lin relates to obstructing agents such as blood clots, cell clusters and normal tissue as causing occlusion of the catheter at its proximal end. There is no mention of antimicrobial or drug based implantable medical devices such as catheters or shunts in an attempt to alleviate occlusion of the catheter lumen caused by biofilm formation through bacterial colonization or occlusion by tissue proliferation.

Accordingly, there exists a need for fluid management flow implants, such as shunts and catheter shunt systems that minimize or eliminate the risk of blockage or obstruction in the implant and reduces the possibility of bacterial biofilm or tissue occlusion within the lumens and inner surfaces of the implants.

BRIEF DESCRIPTION OF THE DRAWINGS

FIGS. 2a and 2b depict a comparison showing the perceived benefits of antibiotic or drug release for a catheter with uniform fluid flow distribution through catheter holes compared with non-uniform fluid flow distribution.

SUMMARY OF THE INVENTION

One embodiment of this invention relates to a method of minimizing formation of bacterial biofilm or tissue proliferation in implantable fluid management systems comprising:

a) providing an implant comprising an antimicrobial or drug-eluting catheter having a proximal and distal end;
b) providing a flow distribution enhancing tip at the distal end of the catheter;
c) inserting the distal end of the catheter into an area to be drained;
d) placing the proximal end of the catheter in a selected area inside or outside of the human body; and
e) draining fluid from the area to be drained to the selected area through the catheter.

Another embodiment of this invention relates to a fluid management system comprising:
a) an antimicrobial or drug-eluting device comprising a proximal and distal end; and
b) a flow distribution enhancing tip at the distal end of the device.

DETAILED DESCRIPTION OF PREFERRED EMBODIMENTS OF THE INVENTION

The present invention is directed toward fluid management flow implants such as catheter drainage devices, preferably hydrocephalus shunts, which contain antibiotics to prevent or reduce the risk of infection and slime formation in the interior surfaces of the catheter and/or a drug to prevent or minimize tissue growth, combined with a flow distribution enhancing tip. This combination device will potentially minimize the risk of blockage or obstruction of the lumens and inner surfaces of the implants due to either biofilm formation or tissue in-growth and allow a greater chance of uninterrupted fluid flow which will in turn lessen the likelihood for costly revision surgery or procedures.

Lundberg et al.: Presence of vitronectin and activated complement factor C9 on ventriculoperitoneal shunts and temporary ventricular drainage catheters. *J Neurosurg* 1999, 90: 101-108 and Bayston & Penny: Excessive production of mucoid substance by *Staphylococcus* SIIA: a possible factor in colonization of Holter shunts. *Dev Med Child Neurol* 1972: 14 Suppl 27: 25-28 recognized that adhesion of bacteria to an implant surface is a critical initial step in the development of biomaterial-centered infections. Also, F. Gotz and G. Peters: Colonization of Medical Devices by Coagulase-Negative Staphylococci. In: *Infections Associated with Indwelling Medical Devices*. F. A. Waldvogel and A. L. Bisno eds., ASM Press, Washington, D.C., 2000, p. 69. report that ventricular CSF cultures in patients with symptoms of shunt infection are frequently negative and the shunt cultures are positive, indicating shunt colonization is a key element of shunt-related infections. The primary adhesion event is mediated by binding proteins on the bacterial surface. Bactiseal catheters are specifically designed to provide extended protection from colonization of the silicone surface by coagulase-negative bacteria such as S epidermidis.

Figure 1A:
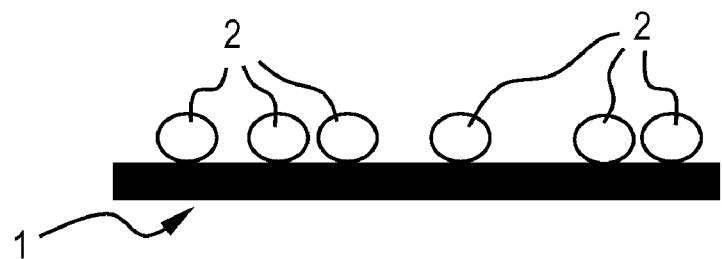
FIG. 1a depicts the first step in staphylococcal biofilm formation that of adhesion of staphylococcal cells to a surface.
Figure 1B:
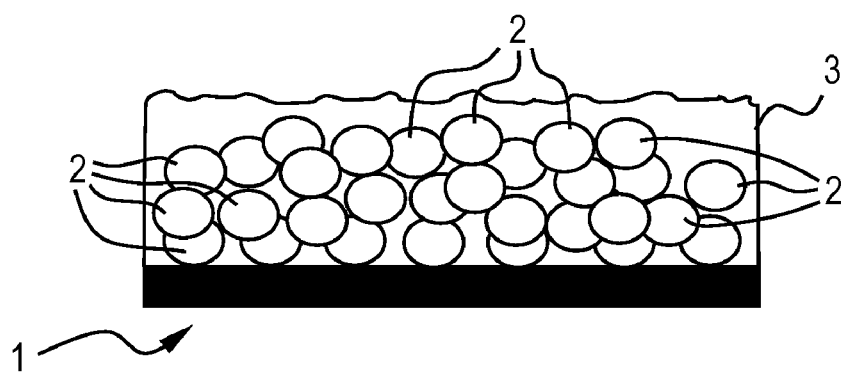
FIG. 1b depicts the second step in staphylococcal biofilm formation, that of multiplication of cells and production of a slime matrix.

FIGS. 1a and 1b describe the above described two step model of biofilm formation. FIG. 1a shows the first step in biofilm formation which is the adherence of the bacterial cells 2 to a surface 1. In FIG. 1b, the second step is the imbedding of the cells 2 into a thick slime matrix (biofilm) 3.

The flow distribution enhancing tip may be any type of tip that enables uniform flow patterns within the medical device. For example, in the case of a catheter, tip designs that help promote uniform flow distribution within the catheter are contemplated. The terms "uniform flow pattern" or "uniform flow distribution" are intended to describe a tip which improves fluid flow over tips not so designed. By providing more uniform fluid flow in the implants, particularly with in the lumens of catheters and hydrocephalus shunts, more uniform release of antimicrobial agents and drugs are achieved which in turn should provide improved resistance to flow occlusion caused by bacterial biofilms and tissue proliferation.

FIGS. 2a and 2b depict the perceived benefit of a flow enhancing tip used in combination with antimicrobial agents and/or drugs compared with antimicrobial agents and/or drugs not combined with a flow enhancing tip.

Referring to FIG. 2a, tip 10 is shown with apertures 12 of varying cross-sectional area. As one proceeds from the distal end to the proximal end of tip 10, apertures 12 decrease in cross-sectional area. This aperture geometry helps to promote uniform flow which in turn is expected to promote uniform release of antimicrobial agents or drugs 14.

In contrast, and now referring to FIG. 2b, conventional tip 10 is shown with apertures 12 of constant cross-sectional area. Fluid flow entering through apertures 12 will not produce a uniform flow with tip 10 and therefore release of antimicrobial agents or drugs 14 is not expected to be uniform.

Examples of suitable flow distribution enhancing tips may be found. For example, in US 2003/0216710 and Lin, infra, the disclosures of which are hereby incorporated by reference.

Figure 3:
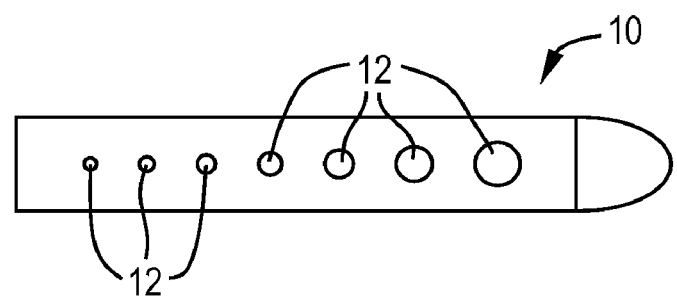
FIG. 3 depicts an embodiment of a fluid flow enhancing distribution tip.

More specifically, Lin, infra, discloses theoretical and experimental data showing that more than 80% of total fluid mass flows into the two most proximal holes of a hydrocephalus shunt. Catheters with variable sized holes, with its largest one situated at the catheter tip, would redistribute the flow more evenly along the entire length of the catheter. Therefore, favorable changes in the geometry of the proximal catheter can significantly alter the fluid dynamics of the catheter, which in itself may ultimately lead to a decrease in the rate of proximal catheter obstruction and when coupled with antimicrobial agents and/or drugs and provide more even release of the antimicrobial agents and/or drugs to more effectively combat bacterial biofilms and/or tissues proliferation. Thus, an example of a suitable tip geometry comprises a tip with a hole pattern of varying hole size where the largest hole is at the distal end of the catheter tip and the smallest hole in the pattern is closest to the shunt valve. Most preferred is a whole geometry as depicted in FIG. 3 wherein the size of the holes progressively increase in cross-sectional area from the most proximal inlet hole to the most distal inlet hole.

In one embodiment, the flow enhancing tip may further comprise a porous device that is incorporated into or onto the tip to reduce the likelihood of blockage by tissue ingrowth. The device may also be used to dialyze the fluid surrounding the catheter. It is envisioned that the pores would be less than 5 μm in their largest dimension, and preferably less than 1 μm, to prevent tissue structures and a supporting blood supply from growing into the luminal space. The device may be attached to the outside surface of the catheter, or it may be inserted into the lumen. Alternatively, the device may be integrated into the catheter material in such a way as to produce a composite structure.

The porous device may have pore sizes of subnano-, nano- or microporosity to selectively exclude blood vessels, cells, biological debris or molecules of a specific size from the lumen of the catheter. The purpose of the porous aspect of the device is also to prevent catheter obstruction due to tissue ingrowth. The device may also be used to dialyze the fluid surrounding the catheter.

The porous device may be attached to the inside and/or outside surfaces of all or part of the catheter. The device may also be incorporated into the catheter material on may comprise a sleeve which fits over a catheter tip. The pore size is ideally less than 1 μm to prevent cellular migration into the lumen of the catheter and the development of tissue structures and a supporting blood supply. The porous device described in this invention may also be used to prevent blockage at the proximal or distal end of a hydrocephalus catheter, or at the outlet of a drug delivery catheter, or at the end of another fluid management catheter. The pore size of the device may also be chosen such that only molecules of a specific size range are allowed to pass into the catheter.

The porous device may be fabricated from metal, ceramic, a selected bulk polymer or a polymer film. The pores may be created by manufacturing processes including but not limited to laser drilling, chemical etching, controlled sintering, or incorporating leachable additives or pore-forming agents.

The fluid discharge from the devices of this invention may be to selected areas inside or outside of the human body. Typical selected discharge areas inside the human body include the peritoneum, the right atrium of the heart, the pleural cavity, and the bladder. The common selected discharge areas outside the human body include fluid collection chambers such as drainage bags.

As used herein, antimicrobial agents are intended to encompass those agents that prevent or minimize bacterial colonization and are intended to include but not be limited to antibiotics, antiseptics and disinfectants.

Examples of suitable antibiotics include tetracyclines (e.g., minocycline), rifamycins (e.g., rifampin), macrolides (e.g., erythromycin), penicillins (e.g., nafcillin), cephalosporins (e.g., cefazolin), other beta-lactam antibiotics (e.g., imipenem, aztreonam), aminoglycosides (e.g., gentamicin), chloramphenicol, sulfonamides (e.g., sulfamethoxazole), glycopeptides (e.g., vancomycin), quinolones (e.g., ciprofloxacin), fusidic acid, trimethoprim, metronidazole, clindamycin, mupirocin, polyenes (e.g., amphotericin B), azoles (e.g., fluconazole) and beta-lactam inhibitors (e.g., sulbactam).

Examples of preferred antibiotics include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin.

Examples of antiseptics and disinfectants are hexachlorophene, cationic bisiguanides (e.g., chlorhexidine, cyclohexidine) iodine and iodophores (e.g., povidone-iodine), para-chloro-meta-xylenol, triclosan, furan medical preparations (e.g., nitrofurantoin, nitrofurazone), methenamine, aldehydes (glutaraldehyde, formaldehyde) and alcohols.

The most preferred antimicrobials are rifampin and clindamycin hydrochloride. Together they provide superior penetration and persistent antimicrobial activity in devices treated. The antimicrobial activity covers most strains of gram-positive bacteria causing the majority of infections in medical devices such as hydrocephalus shunts.

As used herein, the term drugs are intended to encompass drugs that prevent or minimize tissue growth whether the drugs are cytostatic drugs or cytotoxic drugs.

Non-limitative examples of drugs include therapeutic and pharmaceutic agents including: anti-proliferative/antimitotic agents including natural products such as vinca alkaloids (e.g., vinblastine, vincristine, and vinorelbine), paclitaxel, epidipodophyllotoxins (e.g., etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) ll$_b$/lll$_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (e.g., estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives e.g., aspirin; para-aminophenol derivatives e.g., acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), mycophenolic acids, enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

A preferred cytostatic drug is sirolimus (rapamycin) particularly in combination with mycophenolic acid.

A preferred cytotoxic drug is paclitaxel.

Non-limiting examples of fluid flow control devices and systems include catheters, shunts, hydrocephalus shunts, central nervous catheters, dialysis grafts, and ear drainage tubes.

While many types of methods may be used to combine an antimicrobial agent or drug with the fluid flow control system of the present invention such as by coating or impregnation, impregnation is preferred when dealing with medical devices made of polymeric materials such as silicone elastomers.

U.S. Pat. No. 4,917,686 describes a preferred method of incorporating antimicrobial agents within medical devices and such disclosure is hereby incorporated by reference.

The antimicrobial agent and/or drug may also be coated on the inside and/or outside surfaces of all or part of the implant. The drug may be incorporated into the catheter material such that it diffuses from the inside and/or outside surfaces of the tip of the catheter in the region where the fluid drainage holes are located. Alternatively, a porous or other type of sleeve, made from a material that contains the drug(s) may be placed over the outside and/or into the inside lumen of the proximal tip of the catheter in the region where the fluid drainage holes are located.

The impregnation process can be altered to leave an antimicrobial agent and/or drug on the surface. A top-coat that can be used to modulate the elution profile from either the surface or the bulk of the catheter and/or localize the effect of the drug is also being explored. The top-coat can range from a monolayer to a thick layer of synthetic polymer or protein, carbohydrate, or glycoprotein. The coatings can comprise combinations of the previous classes of molecules. In addition, grafted molecules consisting of combinations of synthetic and natural polymers can be used in the form of dendrimers, star, comb or block copolymers. The top-coat can contain drug or could be drug free. Both hydrophilic and or hydrophobic synthetic polymers could be used. For example polyethylene oxide based polymer systems have been widely used as coatings as have fluorinated polymers and copolymers. Layered systems could provide special benefits. Heparin-based polymer systems as well as other sulfated proteoglycan systems (such as chondroitin sulfate) have also been widely used as coatings. Topcoats consisting of laminated layers of these constituents are also contemplated. Such topcoats could be used to reduce the rate of drug elution or provide an immediate burst of particular drugs.

Spatially unhomogeneous topcoats are also described here. These systems can consist of thicker topcoat layers in the vicinity of drainage orifices or have different materials printed in layers onto different points along the surface of the catheter tip. In addition, different drugs or different concentrations of drugs can be laid down at different points along the surface of the catheter tip. The goal would be to produce local effects at the orifices in the catheter tip and may be advantageous where very expensive drugs or polymer materials are being used.

Antiomicrobial agents or drugs can be both physically entrapped as well as covalently grafted in the topcoat layers. Covalently grafted drugs would either inhibit cell attachment by interfering with cell membrane function or would be slowly released by cleavage of labile linkages. Cleavage could either be by chemical or proteolytic mechanisms.

Numerous processes for depositing drug or coatings may be used in conjunction with this invention. Most simply, antimicrobial agent(s) and/or drug(s) are impregnated into the bulk of the catheter either by compounding-in the drug when the catheter is molded (if the drug is stable to this process) or by impregnating the catheter with drug post-molding. Impregnation can be accomplished by using a solvent or co-solvent system to swell the polymer and diffuse-in the antimicrobial agents/drugs, followed by evaporation of the solvents to entrap the antimicrobial agent/drugs. Impregnation by supercritical fluids or supercritical fluid-organic co-solvent fluids is also described to reduce the quantity of organic solvent needed. The advantage here is primarily ecological (reduced toxic pollutants), but also unique drug-polymer microstructures and release-profiles are possible. By limiting the exposure time of the catheter to the antimicrobial agent/drug-solvent solution, an antimicrobial agent/drug loading profile that varies through the thickness of the coating can be achieved. This type of process can provide higher surface concentrations of the antimicrobial agents/drugs. In addition to depositing the antimicrobial agents/drugs in the bulk of the catheter, antimicrobial agents/drugs can also be included in a sprayed-on coating or dip-coated topcoat. Surface variable coatings can be achieved by masking the implants such as catheters in a spraying process or by selectively spraying only certain areas. Selective material layers can be added by sequentially building up different layers. Finally, coatings can be applied or modified using chemical vapor deposition or plasma coating processes. This can also be desirable for preventing delamination of laminated coatings.

It should be understood that the foregoing disclosure and description of the present invention are illustrative and explanatory thereof and various changes in the size, shape and materials as well as in the description of the preferred embodiment may be made without departing from the spirit of the invention.

What is claimed is:

1. A method of minimizing formation of bacterial biofilm or tissue proliferation in implantable fluid management systems comprising:
   a. providing an implant comprising an antimicrobial or drug-eluting catheter having a proximal and distal end;
   b. providing a flow distribution enhancing tip at the distal end of the catheter, wherein the flow distribution enhancing tip includes at least three inlet apertures that progressively increase in cross-sectional area from the most proximal inlet aperture to the most distal inlet aperture;
   c. providing a filter inserted in or around the flow distribution enhancing tip;
   d. inserting the distal end of the catheter into an area to be drained;
   e. placing the proximal end of the catheter in a selected area inside or outside of the human body; and
   f. draining fluid from the area to be drained to the selected area through the catheter.

2. The method of claim 1, wherein the flow distribution enhancing tip comprises a distal end which is sealed and a plurality of inlet apertures located between the distal and proximal ends of the tip.

3. The method of claim 1 wherein the antimicrobial catheter comprises an antimicrobial agent selected from the group consisting of tetracyclines, rifamycins, macrolides, penicillins, cephalosporins, other beta-lactam antibiotics, aminoglycosides, chloramphenicol, sulfonamides, glycopeptides, quinolones, fusidic acid, trimethoprim, metronidazole, clindamycins, mupirocin, polyenes, azoles, beta-lactam inhibitors and mixtures thereof.

4. The method of claim 3 wherein the antimicrobial agent is selected from the group consisting of isminocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, nystatin and mixtures thereof.

5. The method of claim 3 wherein the antimicrobial agent is selected from the group consisting of rifampin, clindamycin hydrochloride and mixtures thereof.

6. The method of claim 3, wherein the wherein the flow distribution enhancing tip comprises a distal end which is sealed and a plurality of inlet apertures located between the distal and proximal ends of the tip.

7. The method of claim 3, wherein the wherein the flow distribution enhancing tip comprises an inlet aperture geometry wherein the inlet apertures progressively increase in cross-sectional area from the most proximal inlet aperture to the most distal inlet aperture.

8. The method of claim 1 wherein the drug-eluting catheter comprises a drug selected from the group consisting of vinca alkaloids, paclitaxel, epidipodophyllotoxins, anthracyclines, mitoxantrone, bleomycins, plicamycin (mithramycin) and mitomycin, enzymes; antiplatelet agents; anti-proliferative/antimitotic alkylating agents; anti-proliferative/antimitotic antimetabolites; platinum coordination complexes; hormones; anti-coagulants; fibrinolytic agents; anti-inflammatory steriods, non-steroidal agents; para-aminophenol derivatives; indole and indene acetic acids, heteroaryl acetic acids, mycophenolic acids, enolic acids, nabumetone, gold compounds; immunosuppressives; sirolimus (rapamycin), azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); protease inhibitors and mixtures thereof.

9. The method of claim 1 wherein the drug comprises paclitaxel.

10. The method of claim 1 wherein the drug comprises sirolimus and mycophenolic acid.

11. The method of claim 1 wherein the drug comprises sirolimus.

* * * * *

UNITED STATES PATENT AND TRADEMARK OFFICE
CERTIFICATE OF CORRECTION

| | | |
|---|---|---|
| PATENT NO. | : 8,221,392 B2 | |
| APPLICATION NO. | : 11/931024 | |
| DATED | : July 17, 2012 | |
| INVENTOR(S) | : Alan Dextradeur and Christophe Mauge | |

It is certified that error appears in the above-identified patent and that said Letters Patent is hereby corrected as shown below:

Title Page, item (63), please insert:

--Application No. 11/931,024 is a continuation of Application No. 10/955,776, filed September 30, 2004.--

Signed and Sealed this
Twenty-ninth Day of January, 2013

David J. Kappos
*Director of the United States Patent and Trademark Office*